(12) United States Patent
Lörner et al.

(10) Patent No.: US 11,371,871 B2
(45) Date of Patent: Jun. 28, 2022

(54) SENSOR UNIT, FLUID POWER UNIT WITH SENSOR UNIT AND METHOD FOR MEASURING PARAMETERS OF A FLUID

(71) Applicant: HAWE Hydraulik SE, Aschheim (DE)

(72) Inventors: Gerhard Lörner, Zorneding (DE); Markus Neumair, Pliening (DE)

(73) Assignee: HAWE Hydraulik SE, Aschheim (DE)

( * ) Notice: Subject to any disclaimer, the term of this patent is extended or adjusted under 35 U.S.C. 154(b) by 320 days.

(21) Appl. No.: 16/748,154

(22) Filed: Jan. 21, 2020

(65) Prior Publication Data
US 2020/0232837 A1    Jul. 23, 2020

(30) Foreign Application Priority Data

Jan. 21, 2019   (DE) .................... 10 2019 200 703.1

(51) Int. Cl.
*G01F 23/263* (2022.01)
*F15B 19/00* (2006.01)
(Continued)

(52) U.S. Cl.
CPC ............ *G01F 23/268* (2013.01); *F15B 19/00* (2013.01); *G01N 27/24* (2013.01); *G01N 33/2858* (2013.01)

(58) Field of Classification Search
CPC ....... G01F 23/268; F15B 19/00; G01N 27/24; G01N 33/2858
See application file for complete search history.

(56) References Cited

U.S. PATENT DOCUMENTS 5,447,056 A * 9/1995 Foote .................. G03G 15/105
                                                         73/304 R
9,810,567 B2 * 11/2017 Mears .................. G01F 23/266
(Continued)

FOREIGN PATENT DOCUMENTS

DE            4312432 A1    10/1994
DE       102013112025 A1     4/2015
(Continued)

OTHER PUBLICATIONS

Japan Patent Office, Notice of Reasons for Rejection issued in corresponding Japanese application No. 2020-006701, dated Nov. 24, 2020, 9 pp.

*Primary Examiner* — David L Singer
*Assistant Examiner* — Fatemeh Esfandiari Nia
(74) *Attorney, Agent, or Firm* — Dinsmore & Shohl LLP

(57) ABSTRACT

A sensor unit is described for measuring parameters of a fluid, in particular a hydraulic fluid, in a fluid power unit, in particular a hydraulic power unit, as well as a fluid power unit with a sensor unit and a method for measuring parameters of a fluid in a fluid power unit. The sensor unit has a contact module and two electrode pairs with two electrodes each. The electrode pairs are connected to the contact module and the longitudinal axes of the electrode pairs are arranged essentially perpendicular to each other. This enables capacitive fluid level measurements with different orientations of the sensor unit without the need to adjust the sensor system. The additional measurement of other parameters of the fluid by means of the method efficiently allows for statements about the quality of the fluid to be made.

17 Claims, 4 Drawing Sheets

(51) Int. Cl.
*G01N 27/24* (2006.01)
*G01N 33/28* (2006.01)

(56) References Cited

U.S. PATENT DOCUMENTS

| | | |
|---|---|---|
| 2007/0107513 A1 | 5/2007 | Tung et al. |
| 2018/0202989 A1 | 7/2018 | Sun et al. |
| 2022/0026031 A1* | 1/2022 | Chen ........................ F21S 4/15 |

FOREIGN PATENT DOCUMENTS

| | | |
|---|---|---|
| DE | 102016010669 A1 | 3/2018 |
| DE | 102016218178 A1 | 3/2018 |
| DE | 102018201562 A1 | 8/2018 |
| JP | H11108735 A | 4/1999 |
| JP | 2004-279232 A | 10/2004 |
| JP | 2009258035 A | 11/2009 |

* cited by examiner

SENSOR UNIT, FLUID POWER UNIT WITH SENSOR UNIT AND METHOD FOR MEASURING PARAMETERS OF A FLUID

CROSS-REFERENCE TO RELATED APPLICATION

This application claims priority from German Application No. 10 2019 200 703.1 filed Jan. 21, 2019, the entire content of which is incorporated herein by reference.

FIELD OF THE INVENTION

The present invention relates to a sensor unit for measuring parameters of a fluid, in particular a hydraulic fluid, in a fluid power unit, in particular a hydraulic power unit, a fluid power unit with a sensor unit according to the invention and a method for measuring parameters of a fluid in a fluid power unit with a sensor unit according to the invention.

BACKGROUND OF THE INVENTION

In the field of capacitive fluid level measurement in fluid power units, sensor units are known which can measure parameters of the fluid, such as the level of the fluid in the tank of the fluid power unit, with reference to a defined direction. In other words: The sensor unit can only measure the fluid level if the fluid power unit is installed "the right way round". That is to say, it is conceivable that the fluid power unit is used in a standing or lying position.

For measurement, for example, a rod probe is inserted into the tank from above, forming one electrode of a capacitor. The metallic wall of the tank, in turn, can then be used as the second electrode of the capacitor, so that the capacitance measurable between the two electrodes depends on the level of the fluid and thus allows a statement about the fluid level in the tank. Furthermore, solutions are known in which the distal end of the rod probe can be used as a reference electrode to increase the measuring accuracy by compensating parameter drift. If, however, a power unit with such sensors is operated in a horizontal position so that the attached rod probe protrudes into the tank from the side, the only thing that could be monitored is whether a threshold value has been exceeded or not.

In order to be able to make additional statements about the condition of the fluid, further parameters must be detected. For example, the change in the conductivity of the fluid in combination with the change in permittivity, which is detected in capacitive fluid level measurement, is an important parameter.

SUMMARY OF THE INVENTION

Against this background, the task of the present invention is to show a sensor unit for measuring various parameters of a fluid in a fluid power unit, which can reliably measure the fluid level in the tank as well as various other parameters of the fluid depending on the orientation of the fluid power unit.

This task is solved by a sensor unit according to claim 1. Advantageous further developments are described in the dependent claims.

The sensor unit according to the invention for measuring parameters of a fluid, in particular a hydraulic fluid, in a fluid power unit, in particular a hydraulic power unit, comprises a contact module and two electrode pairs with two electrodes each. The electrode pairs are connected to the contact module and the longitudinal axes of the electrode pairs are arranged essentially perpendicular to each other.

The sensor unit according to the invention has the advantage that, due to the essentially perpendicular orientation of the longitudinal axes of the electrode pairs to each other, the sensor unit can be mounted in the fluid power unit in such a way that, depending on the orientation of the fluid power unit, it can be used to measure parameters of a fluid in the fluid power unit in at least two spatial directions, without the need to adjust the sensor system. This increases the variability of use of both the sensor unit and a fluid power unit in which such a sensor unit is used. By providing two electrode pairs, one can be used as a measuring electrode pair and the other as a reference electrode pair. In this way, a drift of the fluid parameters—for example over time or as a function of temperature—can be compensated for by means of the reference electrode pair. Furthermore, the reference electrode pair can be used to measure other parameters of the fluid.

Advantageously, the electrodes of an electrode pair are designed as twisted single conductors or as a twin stranded wire. This further increases the design flexibility when using the sensor unit and facilitates the installation of the sensor unit in the fluid power unit. In particular, the electrodes are single conductors insulated with Teflon.

It is advantageous if the electrodes are each provided with crimp contacts on at least one end for connection to the contact module. This ensures easy mounting of the electrode pairs on the contact module.

Preferably the lengths of the electrode pairs can be adjusted to the geometry of the fluid power unit. This creates a particularly variable applicability of the sensor unit in different fluid power units, as the sensor unit is, thus, independent of the different internal geometries of different fluid power units and can be individually adjusted to the respective geometry during assembly.

Advantageously, the contact module is molded. This allows the contact module to be mounted in the fluid power unit at a location that is under fluid without affecting the electronics in the contact module. This simplifies the mounting of the sensor unit within the fluid power unit. Alternatively, additional sensors can be accommodated in the contact module in a space-saving manner in order to detect additional parameters of the fluid power unit that cannot be detected by the electrode pairs. For example, a Hall sensor can be used which detects the rotation speed of a motor by means of a magnet attached to the shaft of the motor.

Preferably, depending on the orientation of the sensor unit, one electrode pair is used as a measuring electrode pair and the other electrode pair as a reference electrode pair. The assignment of measuring electrode pair and reference electrode pair to the electrode pairs is automated. This allows the sensor unit to be operated efficiently in different spatial orientations. For the automated assignment, the effect is used that the capacitance changes proportionally to the portion of the electrode that is under fluid. Thus, an electrode pair that is completely in the fluid can be distinguished from an electrode pair that is only partially in the fluid. It is particularly advantageous for this purpose if a one-time calibration without fluid is performed in advance for both electrode pairs, so that an initial reference capacitance is available. It is conceivable that this calibration is already done at the factory, so that no further effort is required from the end user.

Based on this automated assignment, it is determined that the electrode pair completely submerged in fluid is the reference electrode pair. Therefore the other electrode pair is the measuring electrode pair.

It is advantageous if the sensor unit has an oscillator, a multiplexer and a reference capacitor, wherein the oscillator is switchable to the measuring electrode pair, the reference electrode pair or the reference capacitor via the multiplexer. This allows for compensation of the drift of the oscillator parameters over temperature and time, and thus a more accurate measurement of changes in the parameters of the fluid. It is conceivable that an asymmetric relaxation oscillator is used.

The solution of the task is further achieved with a fluid power unit, in particular a hydraulic power unit, according to claim 8. The fluid power unit has a sensor unit according to the invention, a tank, a first support surface and a second support surface. Therein, the sensor unit is arranged in the tank and the first and second support surfaces are arranged essentially perpendicular to each other. During operation, the fluid power unit rests on the first or on the second support surface. Furthermore, the longitudinal axis of one electrode pair is aligned in a first direction which extends essentially parallel to the first and essentially perpendicular to the second support surface. The longitudinal axis of the other electrode pair is aligned in a second direction which extends essentially perpendicular to the first and essentially parallel to the second support surface.

The advantage of the fluid power unit according to the invention is that, when operating in two alternative orientations—resting on the first or the second support surface—the fluid level and other parameters of the fluid in the tank can be measured by the described installation of the sensor unit according to the invention in the tank, without the need to adjust the sensor system.

Advantageously, the electrode pair aligned in the first direction extends essentially completely from the contact module to an opposite wall of the tank. Furthermore, the electrode pair aligned in the second direction extends essentially completely from the contact module to an opposite wall of the tank. This ensures that in both possible orientations of the fluid power unit, the level of the fluid in the tank can be continuously detected by the sensor unit from the contact module using capacitive fluid level measurement. Depending on the mounting of the contact module, there can be areas for which no fluid level measurement is possible. However, these can easily be compensated by software.

Furthermore, the solution of the task is achieved with a method for measuring parameters of a fluid, in particular a hydraulic fluid, according to claim 10 in a fluid power unit described above. Depending on the orientation of the fluid power unit, one electrode pair is used as a measuring electrode pair and the other electrode pair is used as a reference electrode pair. Furthermore, a first electrode of the reference electrode pair is charged at a first frequency via a first, higher resistance and, when a target voltage is reached, the first electrode is discharged via a second, lower resistance. A second electrode of the reference electrode pair is connected at a second frequency to the potential of a supply voltage or to ground. The terms "higher resistance" and "lower resistance" are to be understood here with respect to the relationship of these two resistances to each other. Furthermore, the level of the fluid is determined at the measuring electrode pair by means of capacitive fluid level measurement. According to the invention, the electrode pair completely under fluid is the reference electrode pair and the other electrode pair is the measuring electrode pair.

The method according to the invention has the advantage that not only capacitive fluid level measurements can be carried out with the sensor unit according to the invention, but also changes in the conductivity of the fluid can be measured. This can be used to draw conclusions about contaminations, for example. Contamination, such as metallic abrasion, increases the conductivity. This increase in turn is detected by the method according to the invention and a warning can be issued, for example, to protect the system, that a change of fluid is necessary. Changes in the conductivity of the fluid cause changes in the first frequency, which can be detected. For example, the first frequency increases when the supply voltage is applied to the second electrode of the reference electrode pair and the conductivity of the fluid increases. In contrast, the first frequency decreases when the second electrode of the reference electrode pair is grounded and the conductivity of the fluid increases.

Advantageously, the second frequency is less than or equal to the first frequency. If the second frequency is chosen lower than the first, the measuring accuracy can be increased by averaging several measured values of the first frequency.

According to the invention, the sensor unit automatically recognizes the orientation of the fluid power unit on the basis of the measured values of the electrode pairs and carries out the assignment of the measuring electrode pair and reference electrode pair to the electrode pairs. This allows the fluid power unit to be operated in different orientations without having to adjust the sensor system. This increases the flexibility in the use of the fluid power unit according to the invention.

The first frequency corresponds to the frequency of an oscillator, which charges the first electrode of the reference electrode pair via the first resistance and discharges it via the second resistance. The oscillator can be switched via a multiplexer to the measuring electrode pair, the reference electrode pair or to a reference capacitor. Advantageously, the reference capacitor has a low temperature dependency. This allows for compensation of the drift of the oscillator parameters over temperature and time, and thus a more accurate measurement of changes in the parameters of the fluid. In particular, an asymmetric relaxation oscillator can be used as the oscillator.

The temperature compensation for the measurement of conductivity can also be achieved by means of a built-in temperature sensor.

BRIEF DESCRIPTION OF THE DRAWINGS

In the following, the invention is explained in more detail by means of an embodiment shown in the figures. Here show schematically.

DETAILED DESCRIPTION OF THE INVENTION

Figure 1:
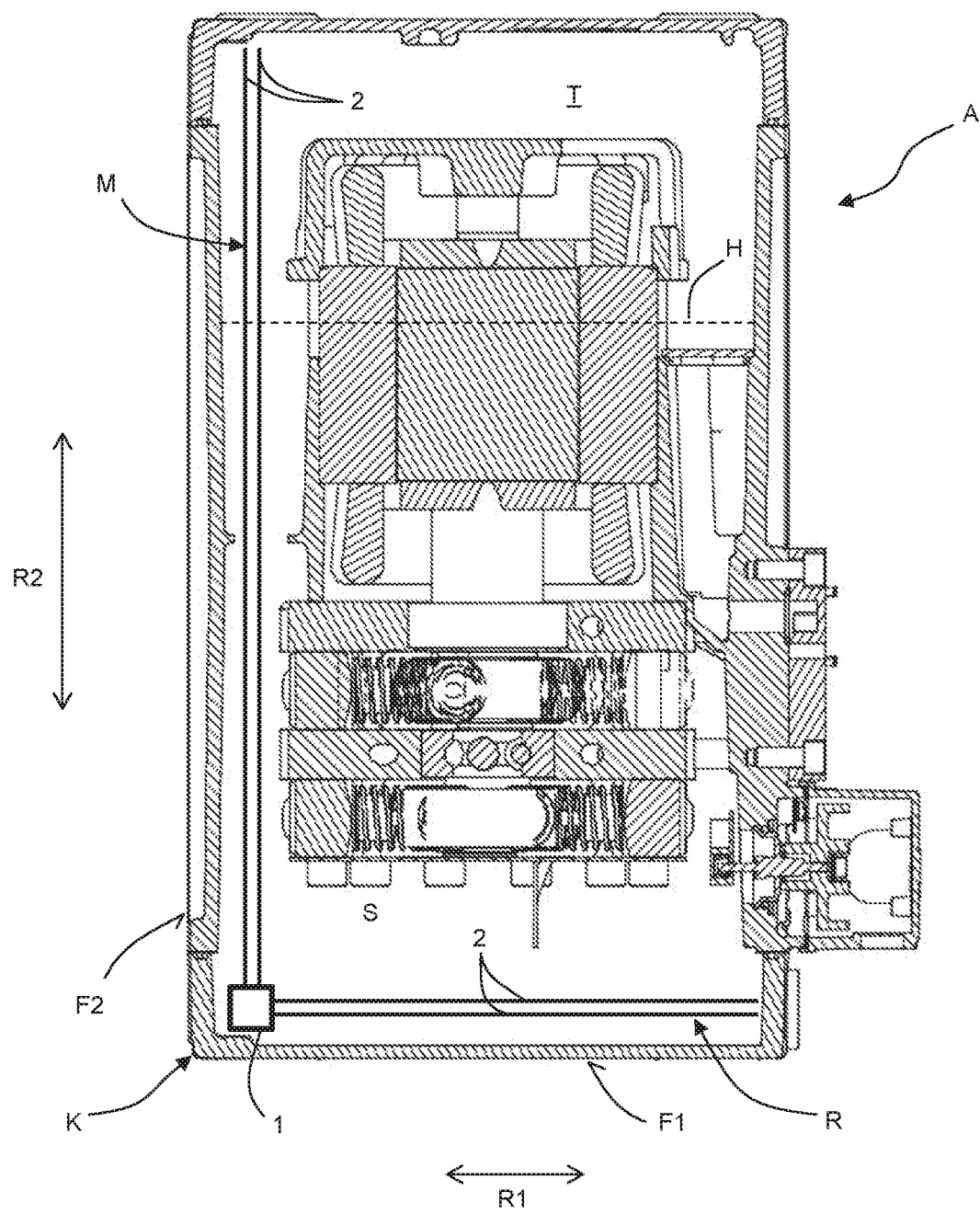
FIG. 1 is a cross-sectional view of fluid power unit in the form of a hydraulic power unit in a first exemplary orientation with a sensor unit according to the invention.
Figure 2:
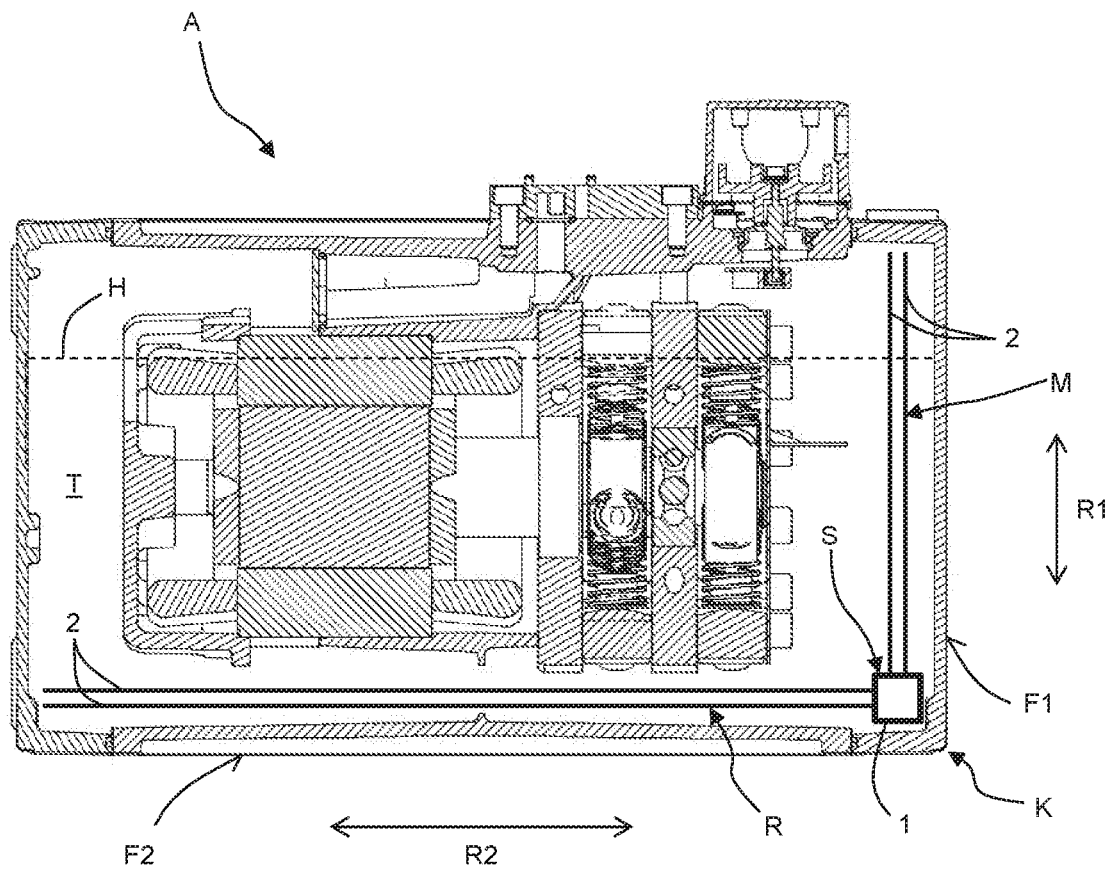
FIG. 2 is a cross-sectional view of the hydraulic power unit shown in FIG. 1 in a second exemplary orientation with a sensor unit according to the invention.

The hydraulic power unit A shown in FIGS. 1 and 2 has a first support surface F1 and a second support surface F2 as well as a tank T. Furthermore, the hydraulic power unit has a sensor unit S, which comprises a contact module 1 and two electrode pairs with two electrodes 2 each. The electrode pairs are connected to contact module 1 and the longitudinal axes of the electrode pairs are arranged essentially perpendicular to each other.

The representation of the electrode pairs in FIGS. 1 and 2 are schematic representations. The electrode pairs are preferably designed as twisted single conductors or as a twin stranded wire, wherein the electrodes 2 are preferably insulated with Teflon. Furthermore, the electrodes are preferably provided with crimp contacts (not shown) for connection to contact module 1.

The longitudinal axis of one electrode pair is aligned in a first direction R1, which is essentially parallel to the first support surface F1 and perpendicular to the second support surface F2. The longitudinal axis of the other electrode pair is aligned in a second direction R2, which is essentially perpendicular to the first support surface F1 and parallel to the second support surface F2.

In the embodiment shown, the contact module 1 is arranged in the area of an inner edge of the tank T, which is closest to a common edge K of the first support surface F1 and the second support surface F2. Of course, the contact module 1 can also be located at another suitable location in the tank T, as explained in more detail below.

The electrode pairs extend from the contact module 1 essentially completely to the opposite wall of tank T in the respective direction R1 or R2. This ensures that in both possible orientations of the hydraulic power unit A the level of a fluid in the tank T, namely a hydraulic fluid H, can be detected by the sensor unit S continuously over the entire respective height of the tank T by means of capacitive fluid level measurement. In the case that the contact module is not, as here, located at an inner edge of the tank T, which is closest to a common edge K of the first support surface F1 and the second support surface F2, any dead zones that may occur with respect to the fluid level measurement in the opposite direction of the measuring direction can be easily compensated by the software. The measuring direction is the direction in which a measuring electrode pair M extends.

Furthermore, the tank T is filled with the hydraulic fluid H up to a fluid level marked with a dotted line in FIGS. 1 and 2.

In the orientation of the hydraulic power unit A shown in FIG. 1, which therein rests on the first support surface F1, the electrode pair aligned in the second direction R2 is a measuring electrode pair M and the electrode pair aligned in the first direction R1 is a reference electrode pair R.

In the orientation of the hydraulic power unit A shown in FIG. 2, which therein rests on the second support surface F2, the electrode pair aligned in the first direction R1 is the measuring electrode pair M and the electrode pair aligned in the second direction R2 is the reference electrode pair R.

The sensor unit S measures the level of the hydraulic fluid H in the tank T of the hydraulic power unit A with the measuring electrode pair M by means of capacitive fluid level measurement. Furthermore, the sensor unit S is additionally able to measure changes in the conductivity of the hydraulic fluid H. This allows for statements to be made about the quality of the hydraulic fluid H and, for example, to determine whether the hydraulic fluid is contaminated to such an extent that it should be replaced.

In applying the measuring method according to the invention, a first electrode of the reference electrode pair R at a first frequency is charged via a first, higher resistance and discharged via a second, lower resistance. This results in the schematic voltage curve shown in FIGS. 3 and 4 as a continuous line.

The second electrode of the reference electrode pair R is connected to either a supply voltage or ground at a second frequency lower than the first frequency. In this way a direct current component between the electrodes can be avoided. If the conductivity of the hydraulic fluid H now changes, this has an effect on the frequency of the voltage curve applied to the first electrode.

Figure 3:
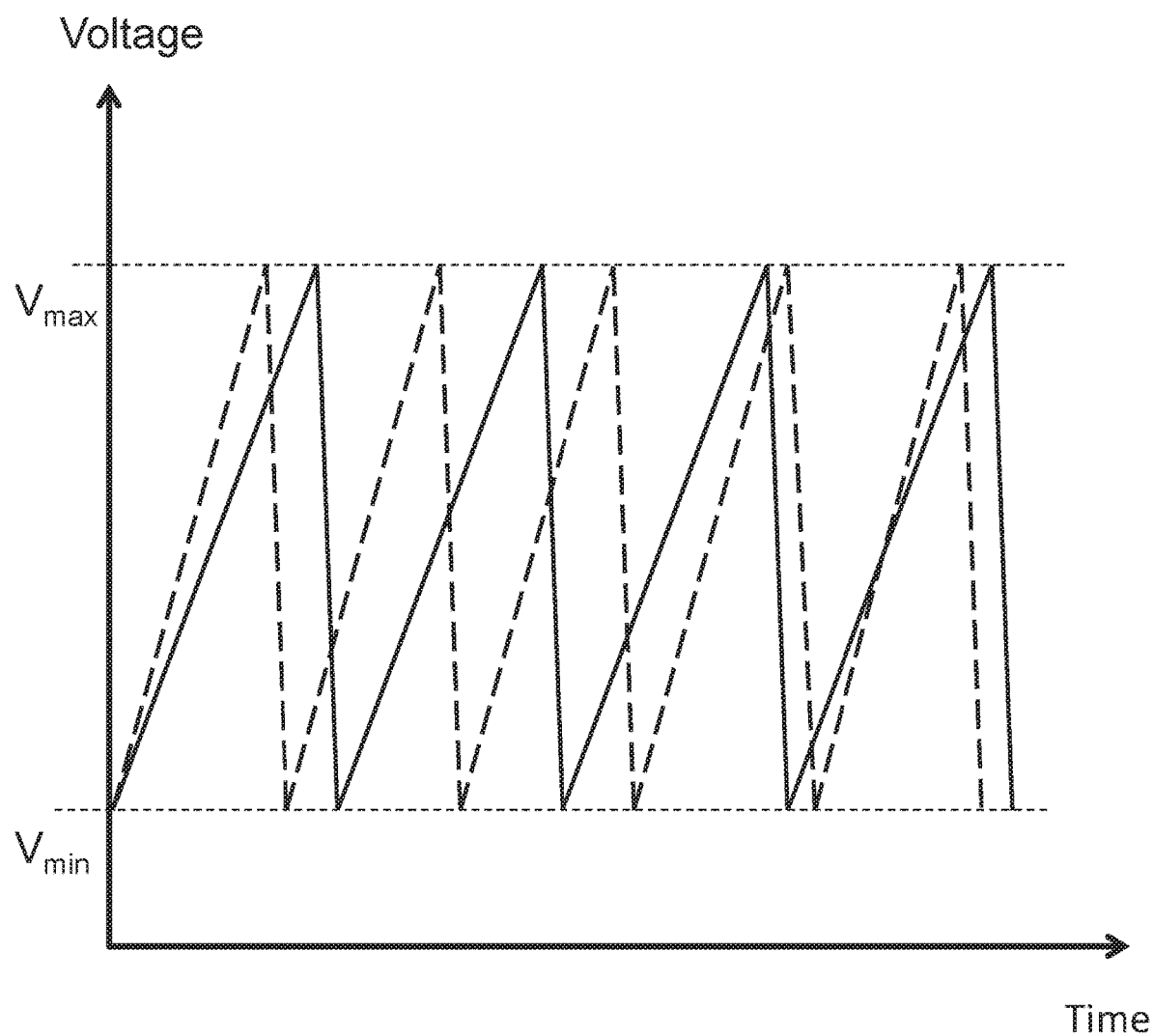
FIG. 3 is a graph showing an exemplary voltage curve at the first reference electrode with high potential at the second reference electrode and increasing conductivity of the hydraulic fluid.

As shown in FIG. 3 as a dashed voltage curve, the first frequency increases in a case where the supply voltage is applied to the second electrode of the reference electrode pair R and the conductivity of the hydraulic fluid increases.

Figure 4:
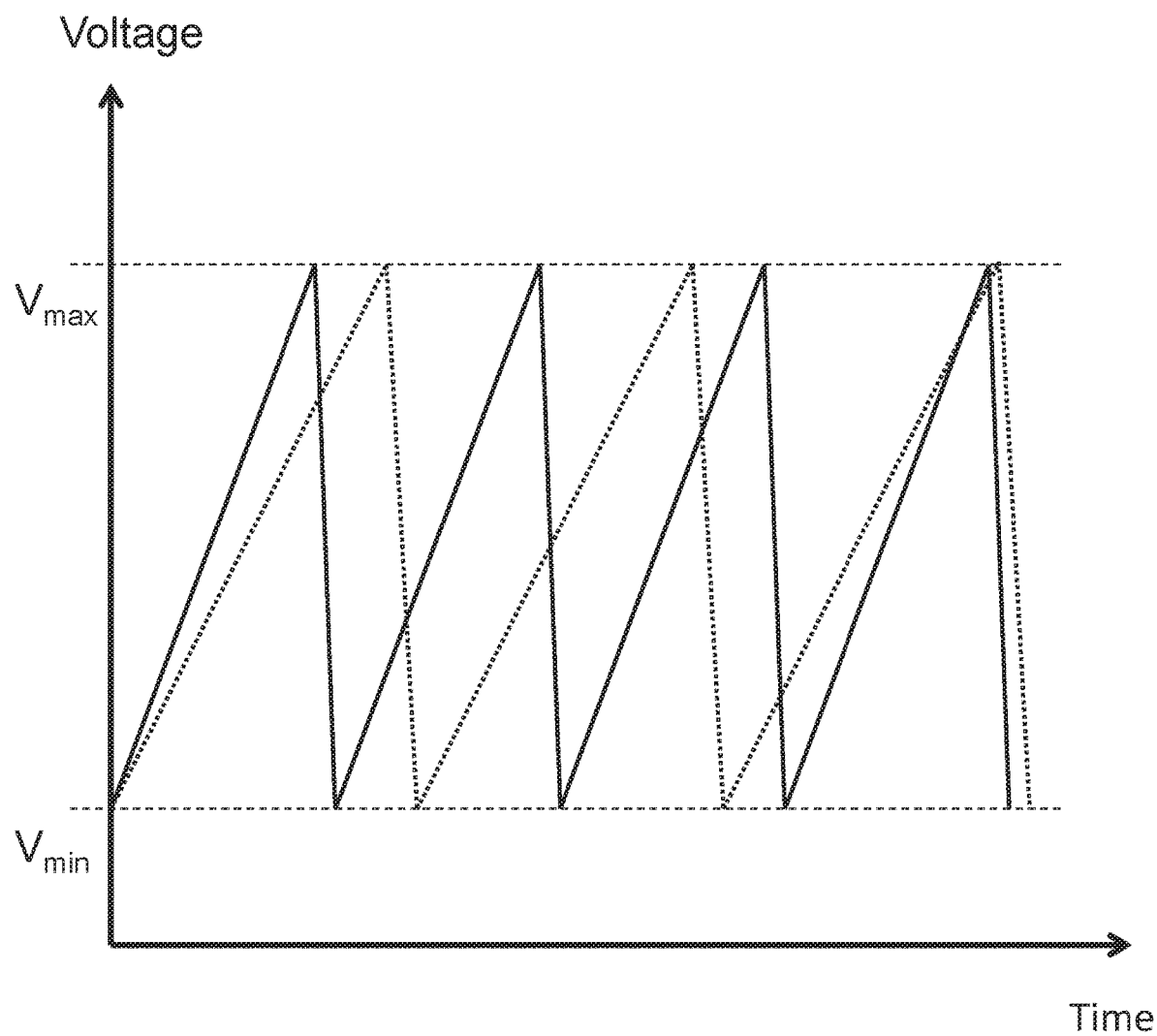
FIG. 4 is a graph showing an exemplary voltage curve at the first reference electrode with low potential at the second reference electrode and increasing conductivity of the hydraulic fluid.

The dotted voltage curve in FIG. 4 shows a case where the second electrode of the reference electrode pair R is connected to ground and the conductivity of the hydraulic fluid H increases. This results in a reduction of the first frequency.

The shift of the first frequency can thus be used to determine whether, for example, contaminations have entered the hydraulic fluid, such as metallic abrasion. It is then conceivable that either a warning signal is given or the power supply to the pump is interrupted to prevent damage to the various components.

As the changes in the conductivity of the hydraulic fluid H and not the absolute conductivity are of interest in the method according to the invention, a time-consuming calibration of the sensor unit is unnecessary.

Furthermore, the sensor unit S has a multiplexer (not shown), an oscillator (not shown) and a reference capacitor (not shown). The oscillator is switched via the multiplexer to the measuring electrode pair M, the reference electrode pair R or to the reference capacitor, so that compensation of the drift of the oscillator parameters over temperature and time and thus a more accurate measurement of the changes in the parameters of the hydraulic fluid H is possible.

REFERENCE NUMERALS 1 contact module
2 electrode
A hydraulic power unit
F1 first support surface
F2 second support surface
H level of the hydraulic fluid
K edge
M measuring electrode pair
R reference electrode pair
R1 first direction
R2 second direction
S sensor unit
T tank

The invention claimed is:
1. A hydraulic power unit, comprising:
   a sensor unit comprising a contact module and two electrode pairs with two electrodes each, the electrode pairs being connected to the contact module and longitudinal axes of the electrode pairs being arranged essentially perpendicular to each other;
   a tank; and
   a first support surface and a second support surface;
   wherein:

the sensor unit is arranged in the tank;
the first and the second support surfaces are arranged essentially perpendicular to each other;
the longitudinal axis of one of the electrode pairs is aligned in a first direction which extends essentially parallel to the first and essentially perpendicular to the second support surface, and the longitudinal axis of the other of the electrode pairs is aligned in a second direction which extends essentially perpendicular to the first and essentially parallel to the second support surface;
the sensor unit is configured to automatically recognize an orientation of the hydraulic power unit on a basis of measured values of the electrode pairs and to assign one of the electrode pairs as a measuring electrode pair and the other of the electrode pairs as a reference electrode pair depending on the orientation of the hydraulic power unit;
a first electrode of the reference electrode pair is configured to be charged at a first frequency via a first, higher resistance and, when a target voltage is reached, the first electrode is configured to be discharged via a second, lower resistance; and
a second electrode of the reference electrode pair is connected to a supply voltage or to ground.

2. The hydraulic power unit according to claim 1, wherein each electrode of at least one of the electrode pairs are twisted single conductors or twin stranded wires.

3. The hydraulic power unit according to claim 1, wherein the electrodes are each provided with crimp contacts on at least one end for connection to the contact module.

4. The hydraulic power unit according to claim 1, wherein lengths of the electrode pairs can be adjusted to a geometry of the hydraulic power unit.

5. The hydraulic power unit according to claim 1, wherein the contact module is molded.

6. The hydraulic power unit according to claim 1, wherein the sensor unit further comprises an oscillator, a multiplexer and a reference capacitor, wherein the oscillator is switchable to the measuring electrode pair or to the reference electrode pair or to the reference capacitor via the multiplexer.

7. The hydraulic power unit according to claim 1, wherein:
the electrode pair aligned in the first direction extends essentially from the contact module to a first wall of the tank opposite the contact module; and
the electrode pair aligned in the second direction extends essentially from the contact module to a second wall of the tank opposite the contact module.

8. A method for measuring parameters of a hydraulic fluid in a hydraulic power unit, comprising providing a hydraulic power unit comprising:
a sensor unit having a contact module and two electrode pairs with two electrodes each, the electrode pairs being connected to the contact module and longitudinal axes of the electrode pairs being arranged essentially perpendicular to each other;
a tank; and
a first support surface and a second support surface;
wherein: the sensor unit is arranged in the tank;
the first and the second support surfaces are arranged essentially perpendicular to each other; and
the longitudinal axis of one of the electrode pairs is aligned in a first direction which extends essentially parallel to the first and essentially perpendicular to the second support surface, and the longitudinal axis of the other of the electrode pairs is aligned in a second direction which extends essentially perpendicular to the first and essentially parallel to the second support surface;
measuring values of the electrode pairs and automatically recognizing an orientation of the hydraulic power unit on a basis of the measured values of the electrode pairs;
automatically assigning one of the electrode pairs as a measuring electrode pair and the other of the electrode pairs as a reference electrode pair depending on the orientation of the hydraulic power unit;
charging a first electrode of the reference electrode pair at a first frequency via a first, higher resistance and, when a target voltage is reached, discharging the first electrode via a second, lower resistance; and
connecting a second electrode of the reference electrode pair to a supply voltage or to ground.

9. The method according to claim 8, wherein:
the supply voltage is connected to the second electrode and has a second frequency which is less than or equal to the first frequency.

10. The method according to claim 8, wherein the first frequency corresponds to a frequency of an oscillator, which charges the first electrode of the reference electrode pair via the first resistance and discharges it via the second resistance, wherein the oscillator is switched via a multiplexer to the measuring electrode pair, the reference electrode pair or to a reference capacitor.

11. A hydraulic power unit, comprising:
a sensor unit comprising a contact module and two electrode pairs with two electrodes each, the electrode pairs being connected to the contact module and longitudinal axes of the electrode pairs being arranged essentially perpendicular to each other;
a tank; and
a first support surface and a second support surface;
wherein:
the sensor unit is arranged in the tank;
the first and the second support surfaces are arranged essentially perpendicular to each other; and the longitudinal axis of one of the electrode pairs is aligned in a first direction which extends essentially parallel to the first and essentially perpendicular to the second support surface;
the longitudinal axis of the other of the electrode pairs is aligned in a second direction which extends essentially perpendicular to the first and essentially parallel to the second support surface; and
the sensor unit is configured to automatically recognize an orientation of the hydraulic power unit on a basis of measured values of the electrode pairs and to assign one of the electrode pairs as a measuring electrode pair and the other of the electrode pairs as a reference electrode pair depending on the orientation of the hydraulic power unit.

12. The hydraulic power unit according to claim 11, wherein each electrode of at least one of the electrode pairs are twisted single conductors or twin stranded wires.

13. The hydraulic power unit according to claim 11, wherein the electrodes are each provided with crimp contacts on at least one end for connection to the contact module.

14. The hydraulic power unit according to claim 11, wherein lengths of the electrode pairs can be adjusted to a geometry of the hydraulic power unit.

15. The hydraulic power unit according to claim 11, wherein the contact module is molded.

16. The hydraulic power unit according to claim 11, wherein the sensor unit further comprises an oscillator, a multiplexer and a reference capacitor, wherein the oscillator is switchable to the measuring electrode pair or to the reference electrode pair or to the reference capacitor via the multiplexer.

17. The hydraulic power unit according to claim 11, wherein:
- the electrode pair aligned in the first direction extends essentially from the contact module to a first wall of the tank opposite the contact module; and
- the electrode pair aligned in the second direction extends essentially from the contact module to a second wall of the tank opposite the contact module.

\* \* \* \* \*